(12) United States Patent
Hayam et al.

(10) Patent No.: US 10,842,399 B2
(45) Date of Patent: Nov. 24, 2020

(54) SYSTEM AND METHOD OF MANAGING ECG DATA FOR USER DEFINED MAP

(71) Applicant: Biosense Webster (Israel) Ltd., Yokneam (IL)

(72) Inventors: Gal Hayam, Kiryat Tivon (IL); Tal Haim Bar-on, Kiryat Tivon (IL); Aharon Turgeman, Zichron Ya'akov (IL); Michael Timofeyev, Nesher (IL)

(73) Assignee: Biosense Webster (Israel) Ltd., Yokneam (IL)

(*) Notice: Subject to any disclaimer, the term of this patent is extended or adjusted under 35 U.S.C. 154(b) by 323 days.

(21) Appl. No.: 15/679,632

(22) Filed: Aug. 17, 2017

(65) Prior Publication Data

US 2019/0053729 A1 Feb. 21, 2019

(51) Int. Cl.
| | | |
|---|---|---|
| A61M 1/00 | (2006.01) | |
| A61B 5/0432 | (2006.01) | |
| G16H 10/60 | (2018.01) | |
| G16H 40/63 | (2018.01) | |
| A61B 5/04 | (2006.01) | |
| A61B 5/0408 | (2006.01) | |
| A61B 5/044 | (2006.01) | |

(52) U.S. Cl.
CPC ............ *A61B 5/0432* (2013.01); *A61B 5/044* (2013.01); *A61B 5/0408* (2013.01); *A61B 5/04012* (2013.01); *G16H 10/60* (2018.01); *G16H 40/63* (2018.01)

(58) Field of Classification Search
USPC ................................................. 600/508–509
See application file for complete search history.

(56) References Cited

U.S. PATENT DOCUMENTS

| | | | |
|---|---|---|---|
| 5,391,199 A | 2/1995 | Ben-Haim | |
| 5,443,489 A | 8/1995 | Ben-Haim | |
| 5,558,091 A | 9/1996 | Acker et al. | |
| 5,916,163 A | 6/1999 | Panescu et al. | |
| 5,934,288 A | 8/1999 | Avila et al. | |

(Continued)

FOREIGN PATENT DOCUMENTS

EP 3192444 A1 7/2017

OTHER PUBLICATIONS

European Search Report for corresponding EPA No. 20180027.3 dated Aug. 10, 2020.

*Primary Examiner* — Nicole F Lavert (57) ABSTRACT

An ECG data management system is disclosed which includes a first memory portion configured to store ECG data having values corresponding to electrical signals of a heart acquired over time via a plurality of electrodes disposed at different areas of the heart. The system also includes a second memory portion configured to store the ECG data and a processing device configured to manage mapping of the ECG data by performing a mapping procedure including generating map data and one or more maps from the ECG data for display; concurrently storing the ECG data in the first memory portion and the second memory portion; and in response to a request to export the ECG data, stopping the storing of the ECG data in the second memory portion and synchronizing the ECG data stored in the second memory portion with the map data while continuing to perform the mapping procedure.

20 Claims, 5 Drawing Sheets

(56) References Cited

U.S. PATENT DOCUMENTS

| | | | |
|---|---|---|---|
| 5,944,022 A | 8/1999 | Nardella et al. | |
| 5,983,126 A | 11/1999 | Wittkampf | |
| 6,172,499 B1 | 1/2001 | Ashe | |
| 6,177,792 B1 | 1/2001 | Govari et al. | |
| 6,266,551 B1 | 7/2001 | Osadchy et al. | |
| 6,456,828 B1 | 9/2002 | Ozluturk | |
| 6,690,963 B2 | 2/2004 | Ben-Haim et al. | |
| 6,788,967 B2 | 9/2004 | Ben-Haim et al. | |
| 2002/0065459 A1 | 5/2002 | MacAdam et al. | |
| 2005/0209525 A1 | 9/2005 | Bojovic et al. | |
| 2009/0069704 A1 | 3/2009 | MacAdam et al. | |
| 2009/0093806 A1 | 4/2009 | Govari et al. | |
| 2009/0099468 A1 | 4/2009 | Thiagalingam et al. | |
| 2009/0138007 A1 | 5/2009 | Govari et al. | |
| 2010/0115002 A1* | 5/2010 | Antinoro | G06F 19/324 707/821 |
| 2010/0298690 A1* | 11/2010 | Scharf | A61B 5/0422 600/407 |
| 2013/0253319 A1* | 9/2013 | Hamilton | A61B 8/5223 600/438 |
| 2014/0107510 A1* | 4/2014 | Bogun | A61B 5/0464 600/516 |
| 2016/0128785 A1* | 5/2016 | Nanthakumar | A61B 5/0422 600/374 |

\* cited by examiner

SYSTEM AND METHOD OF MANAGING ECG DATA FOR USER DEFINED MAP

SUMMARY

Embodiments disclosed herein employ systems and methods which facilitate efficient exporting of stored electrocardiogram (ECG) data, corresponding to ECG signals acquired over time, without stopping a current mapping procedure of storing and mapping the ECG data or waiting for the current mapping procedure to complete. Embodiments also facilitate efficient importing of new data, resulting from the processing of the exported data according to user defined algorithms, to be used by the current mapping procedure to display the new data as a new map.

The present application provides an electrocardiogram (ECG) data management system which includes a first memory portion configured to store ECG data having values corresponding to electrical signals of a heart acquired over time via a plurality of electrodes disposed at different areas of the heart. The system also includes a second memory portion configured to store the ECG data corresponding to the electrical signals. The system also includes a processing device configured to manage mapping of the ECG data by performing a mapping procedure, including generating map data and one or more maps from the ECG data for display, concurrently storing the ECG data in the first memory portion and the second memory portion, and in response to a request to export the ECG data, stopping the storing of the ECG data in the second memory portion and synchronizing the ECG data stored in the second memory portion with the map data while continuing to perform the mapping procedure.

According to an embodiment, the processing device is further configured to manage the mapping of the ECG data by importing new ECG data and comprises new values which replace values of the ECG data corresponding to each of the acquired electrical signals, performing the mapping procedure by generating new map data from the new ECG data and providing the new map data for displaying a new map.

The present application also provides a method of managing ECG data for a user defined map which includes acquiring ECG data corresponding to electrical signals of a heart acquired over time via a plurality of electrodes disposed at different areas of the heart, performing a mapping procedure including generating map data and one or more maps from the ECG data and concurrently storing the ECG data in a first memory portion and a second memory portion. The method also includes, in response to a request to export the ECG data, stopping the storing of the ECG data in the second memory portion and synchronizing the ECG data stored in the second memory portion with the map data while continuing to perform the mapping procedure.

The present application also provides a non-transitory computer readable medium including instructions for causing a computer to execute a computer vision acceleration method. The instructions include acquiring ECG data corresponding to electrical signals of a heart acquired over time via a plurality of electrodes disposed at different areas of the heart and performing a mapping procedure including generating map data and one or more maps from the ECG data. The instructions also include concurrently storing the ECG data in a first memory portion and a second memory portion. The instructions also include, in response to a request to export the ECG data, stopping the storing of the ECG data in the second memory portion and synchronizing the ECG data stored in the second memory portion with the map data while continuing to perform the mapping procedure.

BRIEF DESCRIPTION OF THE DRAWINGS

A more detailed understanding can be had from the following description, given by way of example in conjunction with the accompanying drawings wherein.

DETAILED DESCRIPTION

Recent approaches for treating cardiac arrhythmia (e.g., atrial fibrillation) include minimally invasive ablation procedures (e.g., catheter ablation) in which the heart tissue is ablated to terminate electrical pathways and block faulty electrical impulses that can cause heart rhythm disorders. Conventional methods and systems used for catheter ablation typically include inserting the catheter through an incision in the skin and guided up to the heart. Before ablation is performed, electrocardiogram (ECG) signals of the heart are acquired via electrodes placed at different areas of the heart (e.g., placed via a catheter). For each ECG signal, ECG data is continuously acquired as a plurality of ECG data portions. Each ECG data portion typically corresponds to ECG data acquired over a time interval of about 2.5 seconds. Display maps (e.g., maps of the electro-physical conditions of the heart and maps of the spatio-temporal manifestation of the heart) are generated based on the acquired ECG data to facilitate determination of whether one or more areas of the heart are causing an irregular heart rhythm.

During some ablation procedures, it is desirable to export (i.e., extract) data corresponding to a portion of the recorded ECG signals (e.g., ECG signals currently being displayed), process the export data according to user defined (e.g., physician defined) algorithms and view the results of the processed data as a new map. Conventional techniques for exporting and processing the exported data, however, are cumbersome and time consuming. For example, data cannot be exported while a current mapping procedure is being performed (e.g., map is being generated and displayed). Instead, data corresponding to the ECG signals cannot be exported until after the current mapping procedure is completed or stopped and a new mode (non-mapping procedure mode) is entered to export the data.

Embodiments disclosed herein employ systems, apparatuses and methods which facilitate efficient exporting of stored ECG data, corresponding to currently displayed ECG signals, without stopping a current mapping procedure or waiting for the current mapping procedure to complete. Embodiments facilitate the exporting of ECG data by continuously and concurrently storing the acquired ECG data in a first memory portion of a computing device and a second memory portion that is removable from the computing device. Embodiments also facilitate efficient importing (e.g., insertion into a mapping procedure processing pipeline) of new data (e.g., resulting from the processing of the exported data according to user defined algorithms) to the computing device and displaying the new data as a new map.

Mapping techniques described herein utilize various parameters (e.g., cycle, earliness, R-S complex, conduction velocity (CV), block and fractionation) of acquired ECG signals and detected local activation times (LATs) to identify potential evidence of sources of activation (i.e., drivers) and perpetuators of anatomical substrate (e.g., surface of the heart). Evidence identifying potential drivers (e.g., focal sources and rotational activation patterns (RAPs)) and perpetuators is used to provide the mapping of the AF substrate.

Figure 1:
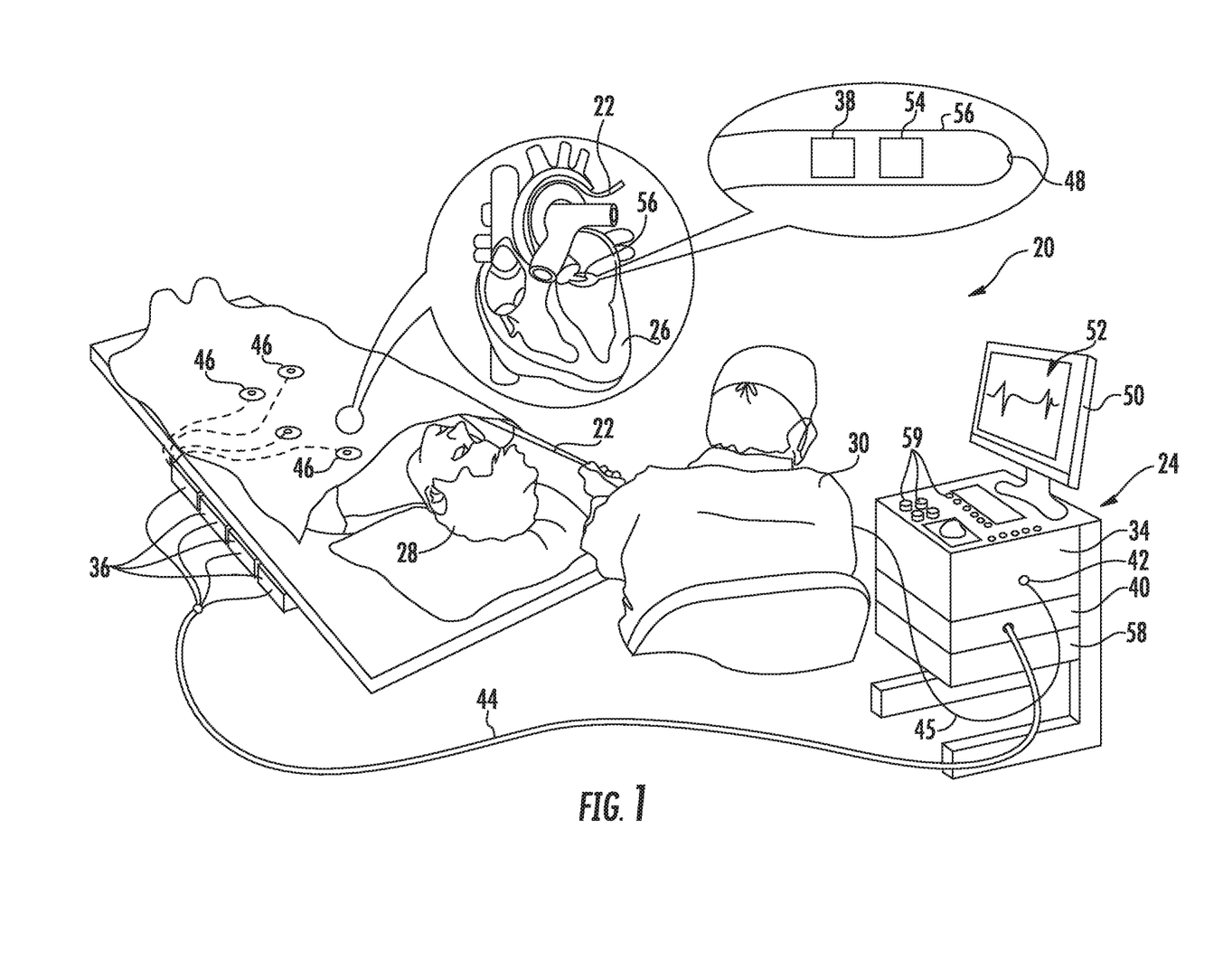
FIG. 1 is an illustration of an example medical system for navigating a tool in 3-D space according to embodiments disclosed herein.

Referring now to FIG. 1, an illustration of an example medical system 20 is shown that may be used to generate and display information 52 (e.g., anatomical models of a portion of a patient and signal information). Tools such as tool 22, can be any tool used for diagnostic or therapeutic treatment, such as for example, a catheter (such as catheter 202 shown in FIG. 2 and described in more detail below) having a plurality of electrodes for mapping electrical potentials in a heart 26 of a patient 28. Alternatively, tools may be used, mutatis mutandis, for other therapeutic and/or diagnostic purposes of different portions of anatomy, such as in the heart, lungs or other body organs, such as the ear, nose, and throat (ENT). Tools may include, for example, probes, catheters, cutting tools and suction devices.

An operator 30 may insert the tool 22 into a portion of patient anatomy, such as the vascular system of the patient 28 so that a tip 56 of the tool 22 enters a chamber of the heart 26. The control console 24 may use magnetic position sensing to determine 3-D position coordinates of the tool (e.g., coordinates of the tip 56) inside the heart 26. To determine the position coordinates, a driver circuit 34 in the control console 24 may drive, via connector, 44, field generators 36 to generate magnetic fields within the anatomy of the patient 28.

The field generators 36 include one or more emitter coils (not shown in FIG. 1), placed at known positions external to the patient 28, which are configured to generate magnetic fields in a predefined working volume that contains a portion of interest of the patient anatomy. Each of the emitting coils may be driven by a different frequency to emit a constant magnetic field. For example, in the example medical system 20 shown in FIG. 1, one or more emitter coils can be placed below the torso of the patient 28 and each configured to generate magnetic fields in a predefined working volume that contains the heart 26 of the patient.

As shown in FIG. 1, a magnetic field location sensor 38 is disposed at the tip 56 of tool 22. The magnetic field location sensor 38 generates electrical signals, based on the amplitude and phase of the magnetic fields, indicating the 3-D position coordinates of the tool (e.g., position coordinates of the tip 56). The electrical signals may be communicated to the control console 24 to determine the position coordinates of the tool. The electrical signals may be communicated to the control console 24 via wire 45.

Alternatively, or in addition to wired communication, the electrical signals may be wirelessly communicated to the control console 24, for example, via a wireless communication interface (not shown) at the tool 22 that may communicate with input/output (I/O) interface 42 in the control console 24. For example, U.S. Pat. No. 6,266,551, whose disclosure is incorporated herein by reference, describes, inter alia, a wireless catheter, which is not physically connected to signal processing and/or computing apparatus and is incorporated herein by reference. Rather, a transmitter/receiver is attached to the proximal end of the catheter. The transmitter/receiver communicates with a signal processing and/or computer apparatus using wireless communication methods, such as IR, RF, Bluetooth, or acoustic transmissions. The wireless digital interface and the I/O interface 42 may operate in accordance with any suitable wireless communication standard that is known in the art, such as for example, IR, RF, Bluetooth, one of the IEEE 802.11 family of standards (e.g., Wi-Fi), or the HiperLAN standard.

Although FIG. 1 shows a single magnetic field location sensor 38 disposed at the tip 56 of tool 22, tools may include one or more magnetic field location sensors each disposed at any tool portion. The magnetic field location sensor 38 may include one or more miniature coils (not shown). For example, a magnetic field location sensor may include multiple miniature coils oriented along different axes. Alternatively, the magnetic field location sensor may comprise either another type of magnetic sensor or position transducers of other types, such as impedance-based or ultrasonic location sensors.

The signal processor 40 is configured to process the signals to determine the position coordinates of the tool 22, including both location and orientation coordinates. The method of position sensing described hereinabove is implemented in the CARTO mapping system produced by Biosense Webster Inc., of Diamond Bar, Calif., and is described in detail in the patents and the patent applications cited herein.

The tool 22 may also include a force sensor 54 contained within the distal end 32. The force sensor 54 may measure a force applied by the tool 22 (e.g., the tip 56 of the tool) to the endocardial tissue of the heart 26 and generate a signal that is sent to the control console 24. The force sensor 54 may include a magnetic field transmitter and a receiver connected by a spring in the distal end 32, and may generate an indication of the force based on measuring a deflection of the spring. Further details of this sort of probe and force sensor are described in U.S. Pat. No. 8,357,152 (formerly U.S. Patent Application Publication No. 2009/0093806) and U.S. Pat. No. 8,535,308 (formerly U.S. Patent Application Publication No. 2009/0138007) whose disclosures are incorporated herein by reference. Alternatively, the distal end 32 may include another type of force sensor that may use, for example, fiber optics or impedance measurements.

The tool 22 may also include an electrode 48 coupled to the tip 56 and configured to function as an impedance-based position transducer. Additionally or alternatively, the electrode 48 may be configured to measure a certain physiological property, for example the local surface electrical potential (e.g., of cardiac tissue) at one or more locations. The electrode 48 may be configured to apply RF energy to ablate endocardial tissue in the heart 26.

Although the example medical system 20 may be configured to measure the position of the tool 22 using magnetic-based sensors, other position tracking techniques may be used (e.g., impedance-based sensors). Magnetic position tracking techniques are described, for example, in U.S. Pat. Nos. 5,391,199, 5,443,489, 6,788,967, 6,690,963, 5,558, 091, 6,172,499 6,177,792, the disclosures of which are incorporated herein by reference. Impedance-based position tracking techniques are described, for example, in U.S. Pat. Nos. 5,983,126, 6,456,828 and 5,944,022, the disclosures of which are incorporated herein by reference.

The I/O interface 42 may enable the control console 24 to interact with the tool 22, the body surface electrodes 46 and any other sensors (not shown). Based on the electrical impulses received from the body surface electrodes 46 and the electrical signals received from the tool 22 via the I/O interface 42 and other components of medical system 20, the signal processor 40 may determine the location of the tool in a 3-D space and generate the display information 52, which may be shown on a display 50.

The signal processor 40 may be included in a general-purpose computer, with a suitable front end and interface circuits for receiving signals from the tool 22 and controlling the other components of the control console 24. The signal processor 40 may be programmed, using software, to perform the functions that are described herein. The software may be downloaded to the control console 24 in electronic form, over a network, for example, or it may be provided on non-transitory tangible media, such as optical, magnetic or electronic memory media. Alternatively, some or all of the functions of the signal processor 40 may be performed by dedicated or programmable digital hardware components.

In the example shown at FIG. 1, the control console 24 is connected, via cable 44, to body surface electrodes 46, each of which are attached to patient 28 using patches (e.g., indicated in FIG. 1 as circles around the electrodes 46) that adhere to the skin of the patient. Body surface electrodes 46 may include one or more wireless sensor nodes integrated on a flexible substrate. The one or more wireless sensor nodes may include a wireless transmit/receive unit enabling local digital signal processing, a radio link, and a miniaturized rechargeable battery. In addition or alternative to the patches, body surface electrodes 46 may also be positioned on the patient using articles worn by patient 28 which include the body surface electrodes 46 and may also include one or more position sensors (not shown) indicating the location of the worn article. For example, body surface electrodes 46 can be embedded in a vest that is configured to be worn by the patient 28. During operation, the body surface electrodes 46 assist in providing a location of the tool (e.g., catheter) in 3-D space by detecting electrical impulses generated by the polarization and depolarization of cardiac tissue and transmitting information to the control console 24, via the cable 44. The body surface electrodes 46 can be equipped with magnetic location tracking and can help identify and track the respiration cycle of the patient 28. In addition to or alternative to wired communication, the body surface electrodes 46 may communicate with the control console 24 and one another via a wireless interface (not shown).

During the diagnostic treatment, the signal processor 40 may present the display information 52 and may store data representing the information 52 in a memory 58. The memory 58 may include any suitable volatile and/or non-volatile memory, such as random access memory or a hard disk drive. The operator 30 may be able to manipulate the display information 52 using one or more input devices 59. Alternatively, the medical system 20 may include a second operator that manipulates the control console 24 while the operator 30 manipulates the tool 22. It should be noted that the configuration shown in FIG. 1 is an example. Any suitable configuration of the medical system 20 may be used and implemented.

Figure 2:
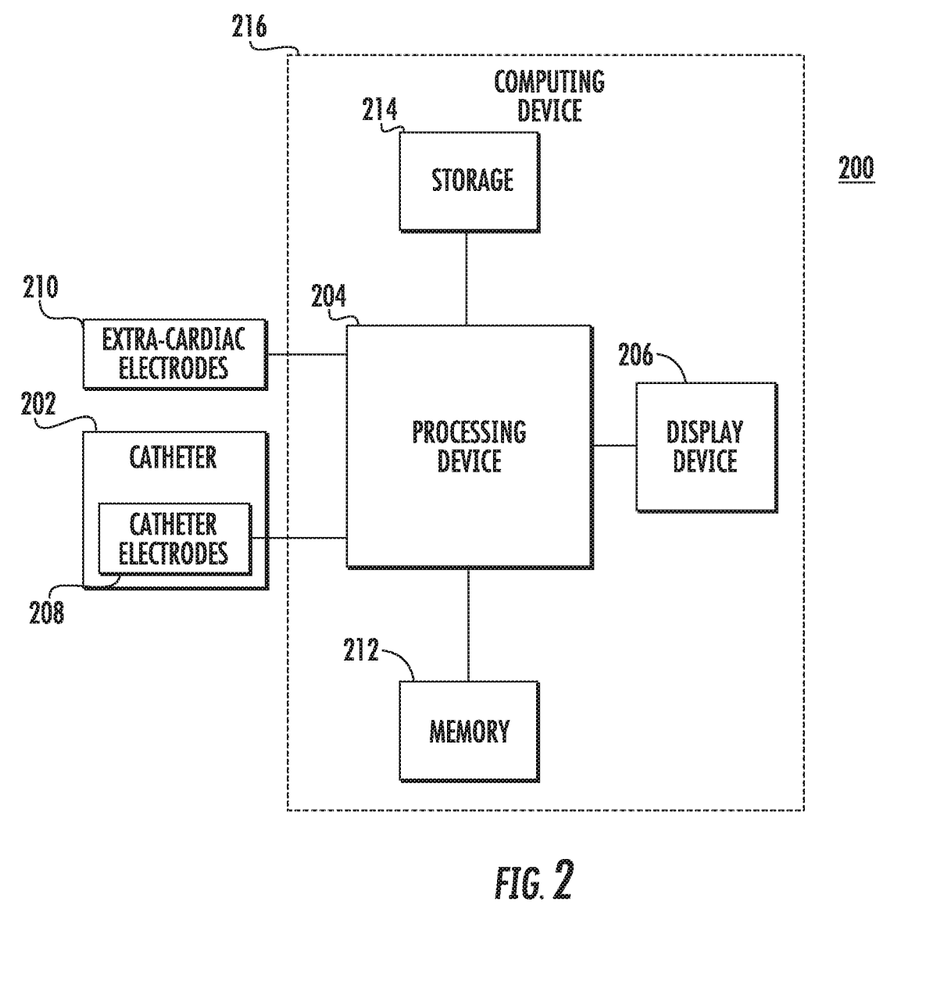
FIG. 2 is an illustration of components of an example medical system for use with embodiments described herein.

FIG. 2 is a block diagram illustrating example components of a medical system 200 for use with embodiments described herein. As shown in FIG. 2, the system 200 includes a catheter 202, a processing device 204, a display device 206 and multiple memory portions, including memory 212 and storage 214 (e.g., removable storage device). As shown in FIG. 2, the processing device 204, display device 206, memory 212 and storage 214 are a part of computing device 216. In some embodiments, display device 206 may be separate from computing device 216.

Catheter 202 may be one of a plurality of different catheter types, such as for example, a basket type catheter. Catheter 202 includes a plurality of catheter electrodes 208 configured to detect electrical activity (i.e., electrical signals) of an area of the heart over time. Catheter 202 is maneuverable to place each catheter electrode 208 at a different area of a heart. When an ECG is performed, each catheter electrode 208 detects the electrical activity of an area of the heart in contact with the electrode 208. The example system 200 also includes extra-cardiac electrodes 210 (e.g., body surface electrodes 46 shown in FIG. 1) configured to detect electrical activity of the heart via detection of electrical changes on the skin due to the electro-physiologic pattern of the heart. Catheter 202, including catheter electrodes 208, and extra-cardiac electrodes 210 may be in wired or wireless communication with processing device 204. In some embodiments, extra-cardiac electrodes 210 may not be used.

Processing device 204 is configured to receive the detected ECG signals from the catheter electrodes 208 and the extra-cardiac electrodes 210, store the ECG signals and provide data corresponding to the ECG signals to the display device 206 for display. For example, processing device 204 may include one or more processors configured to filter ECG signals, fractionate ECG signals into signal components (e.g., slopes, waves, complexes), provide data corresponding to the ECG signals, combine ECG signal information, interpolate mapping information, and record (i.e., store) data corresponding to the ECG signals. The data corresponding to the ECG signals may be provided to memory 212 and storage 214, as described in more detail below.

Display device 206 may include one or more displays each configured to display data corresponding to the ECG signals. For example, display device 206 is configured to display ECG signal information and maps representing a spatio-temporal manifestation of the heart. Display device 206 may be in wired or wireless communication with processing device 204. In some embodiments, display device may be separate from computing device 216.

Memory 212 and storage 214 are examples of different memory portions each used to store data, such as ECG data. Types of memory 212 include volatile and non-volatile memory, such as for example, random access memory (RAM), dynamic RAM, or a cache. Types of storage 214 include fixed storage (e.g., a hard disk drive and a solid state drive) and removable storage (e.g., an optical disk and a flash drive). As described in more detail below, ECG data can be stored in multiple memory portions. For example, ECG data, corresponding to electrical signals of a heart acquired over time via catheter electrodes 208, is stored in a first memory portion, such as memory 212. Further, the ECG data corresponding to the same electrical signals is concurrently stored at a second memory portion, such as storage 214. The data in storage 214 may be processed at other devices (e.g., remote computing devices) according to user defined algorithms, as described in more detail below. In some embodiments data on storage 214 may be wirelessly transmitted via a network.

Figure 3:
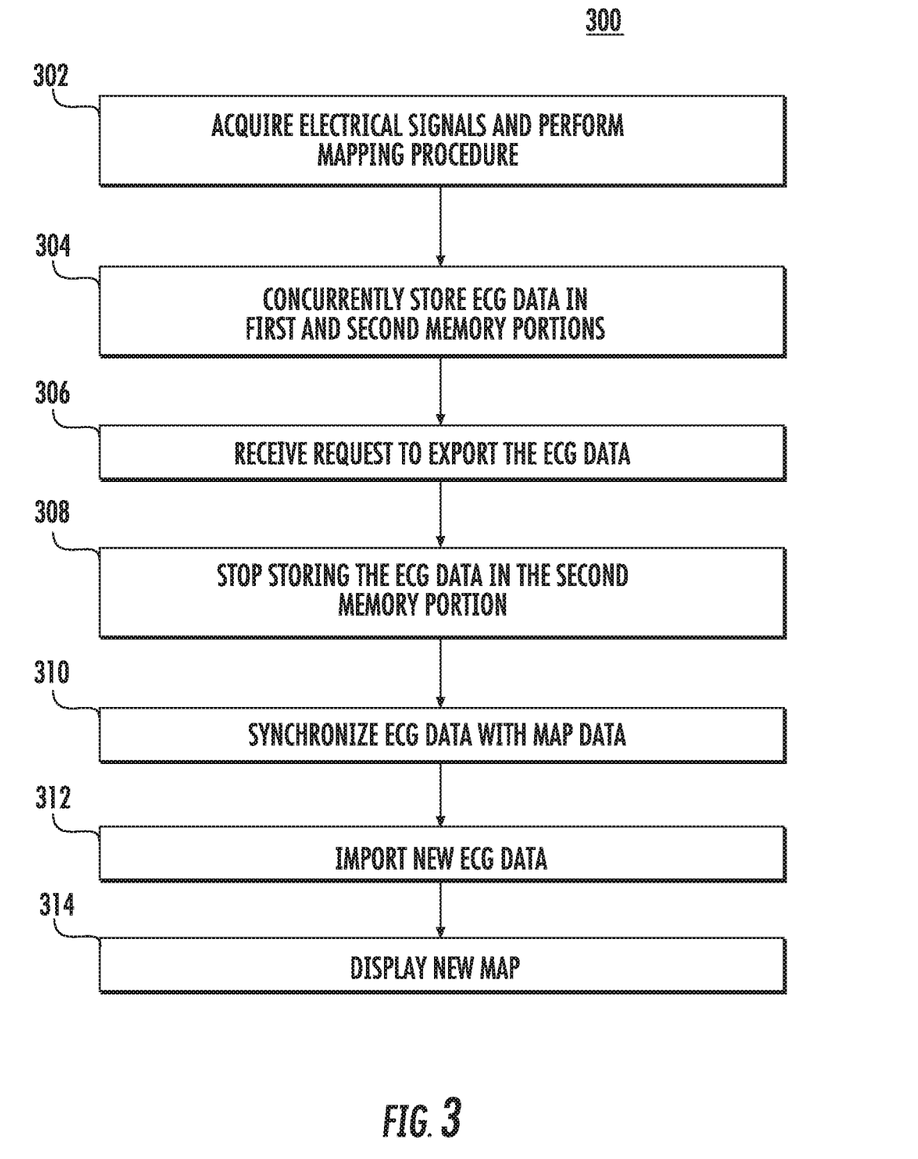
FIG. 3 is a flow diagram illustrating an example method of managing ECG data for a user defined map.

FIG. 3 is a flow diagram illustrating an example method 300 of managing ECG data for a user defined map. As shown at block 302, the method includes starting acquisition of electrical signals over time and starting the performing of a mapping procedure using the acquired electrical signals (i.e., acquired ECG data). That is, the ECG data is acquired via the electrodes disposed at the different areas of the heart. The mapping procedure, which includes generating and displaying map data and one or more maps of the heart, is performed using the acquired ECG data.

Figure 4:
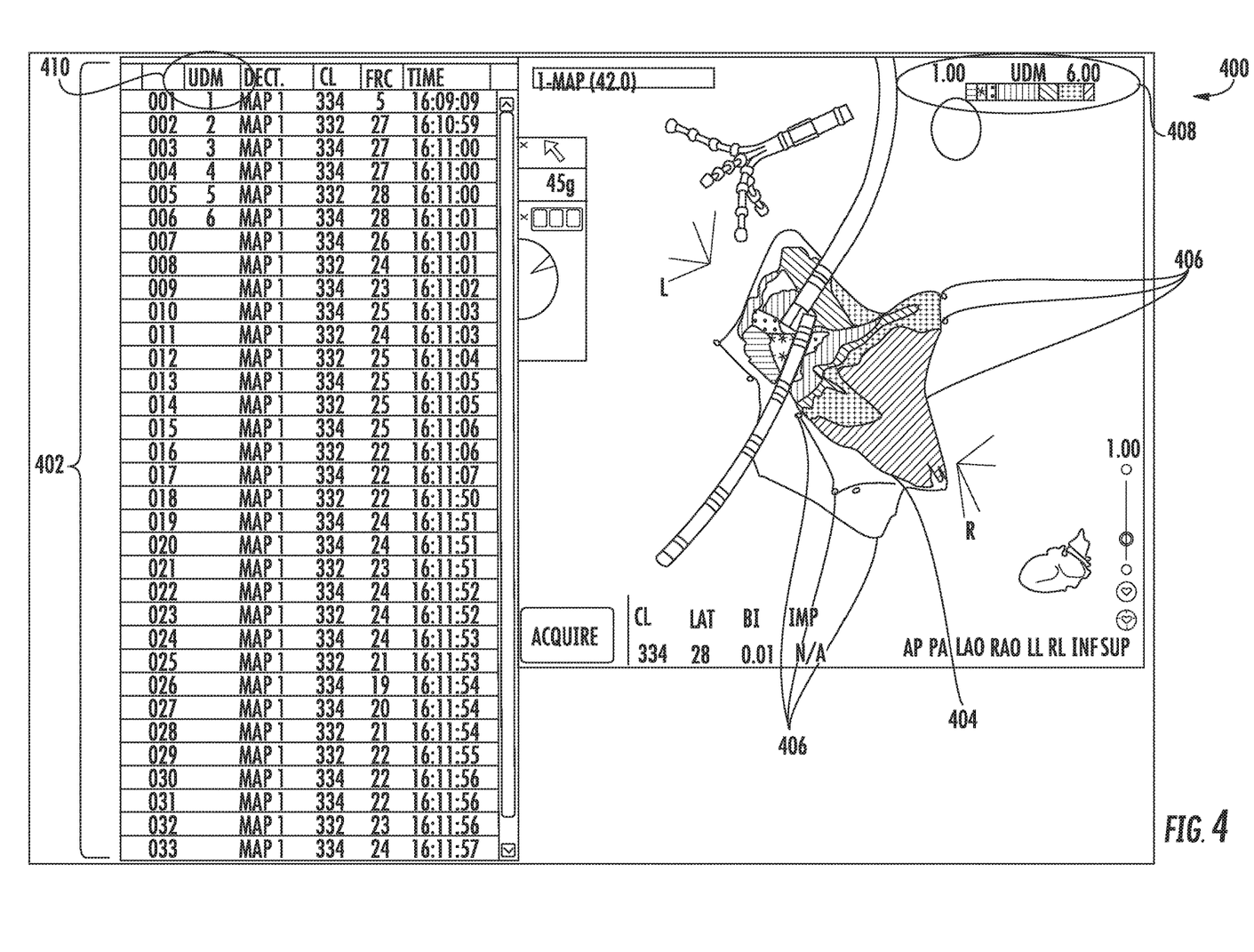
FIG. 4 is a screen shot of example ECG data and a map representing a spatio-temporal manifestation of the heart displayed according to embodiments described herein.

For example, FIG. 4 illustrates an example display 400 of ECG map data 402 and a heart map 404 during a mapping procedure. As shown in FIG. 4, ECG map data 402 is displayed for each acquired signal (e.g., signals 001 to signals 033) and heart map 404 is displayed using the ECG map data 402. Each of the acquired signals (e.g., signals 001 to signals 033) corresponds to points 406 shown at different locations on the heart map 404.

As shown at block 304, the method 300 includes concurrently storing the acquired ECG data in first and second memory portions. For example, ECG data is continuously and currently stored in a first memory portion (e.g., a fixed memory portion) and a second memory portion (e.g., a removable storage device). For each ECG signal, ECG data portions are continuously acquired over time. In conventional techniques, each ECG data portion representing an electrical signal of the heart is acquired from an electrode over a time interval of about 2.5 seconds. The conventional 2.5 second acquisition time interval acquires, on average, ECG data for 2 consecutive heart beats. While 2.5 seconds may be sufficient for clinical practice, external analysis may be facilitated using larger acquisition time intervals. For example, larger acquisition time intervals may provide additional data, which in turn, can provide more accurate maps. The additional acquisition time intervals, however, result in larger amounts of stored data (e.g., in both the first and second memory portions) and longer export times.

Embodiments described herein provide a plurality of selectable acquisition time intervals (e.g., 2.5 seconds to 15 seconds). Accordingly, a user (e.g., a physician) can select one of a plurality of selectable acquisition time intervals based on potential tradeoffs (e.g., larger amounts of stored data and longer export times versus larger amounts of ECG data for each acquisition time interval). In response to the selection, the selected acquisition time interval is used to acquire the ECG data for a mapping procedure. When ECG data is acquired via a first electrode (i.e., corresponding to a first point) for a new study, a folder is created (e.g., "User-DefinedMap" (UDM) folder) on a removable storage device. A temporary sub-folder is created in the UDM folder for each map in the study. For example, when map data is generated for displaying a map of the study, a temporary sub-folder for the map data is created in the UDM folder for the study. When new map data is generated for displaying a new map of the study, a temporary sub-folder for the new map data is created in the UDM folder for the study.

As shown at block 306, the method 300 includes receiving a request to export the ECG data. For example, at any time during the mapping procedure, a request (e.g., a user request via a user interface) may be received to export the ECG data that is being continuously stored in the removable storage. In response to the request to export the ECG data, the UDM folder, which includes the temporary folder having the continuously stored ECG data for the current map, is accessed. The temporary folder may also be named according to the current map and study (e.g., "Map Name>_UDM.txt") with a default LAT value (e.g., plurality of default values of "−10000" shown in FIG. 5).

Additional changes to the currently displayed map, after the ECG data is exported, begin an additional export process. Because the additional export process is longer than the first export process, additional export processes are performed in a review mode, which enables the user to review results from a previous study (i.e., performed when the patient was on the table). The review mode is a retrospective mode in which new data is not acquired and the user can edit existing maps, ECG data, and other data.

Embodiments also include displaying estimated export times to the user. For example, Table 1 (shown below) illustrates the number of minutes (i.e., the export time interval) estimated to export ECG data for different numbers of acquisition points (i.e., 500, 1000 and 3,000) according to different data acquisition time intervals (i.e., ECG time spans of 2.5 seconds, 6 seconds, 10 seconds and 15 seconds).

TABLE 1

Estimated Number of Minutes Required for Additional Export

| | ECG Time Span | | | |
|---|---|---|---|---|
| Points | 2.5 seconds | 6 seconds | 10 seconds | 15 seconds |
| 500 | 1 | 2 | 15 | 17 |
| 1,000 | 2 | 3 | 27 | 33 |
| 3,000 | 7 | 11 | 83 | 99 |

Export time intervals are derived from the ECG data acquisition time interval (i.e., 2.5 seconds, 6 seconds, 10 seconds and 15 seconds in Table 1). That is, as the ECG data acquisition time interval is increased, more data is exported, and therefore, more time is incurred to export the data. For example, as shown in Table 1, an export time interval of 1 minute is estimated to export ECG data for 500 points each having an acquisition point time interval of 2.5 seconds. An export time interval of 99 minutes is estimated to export ECG data for 3,000 points each having a data acquisition point time interval of 15 seconds. The estimated number of minutes shown in Table 1 may be provided to a user. In response to being provided with the estimated number of minutes, a user may set (or modify existing settings) one or more system parameters. For example, if the estimated number of minutes indicate the export time interval will be longer than a desired time interval (e.g., more than 30 minutes), the user may reduce the number of data acquisition points to be displayed or shorten the ECG acquisition time interval.

Embodiments also include providing a user with different export type selections, such as for example, a file type having exported ECG data per point. Export type selections also include a file type which displays data in columns, enabling the user to enter different types of data, such as point indexes, catheter X axis coordinates, catheter Y axis coordinates, catheter Z axis coordinates, catheter azimuths, catheter elevations, catheter roll, unipolar, bipolar, LAT, impedance, force and point start time.

As shown at blocks 308 and 310, the method 300 includes stopping the storing of the ECG data in the first memory portion and synchronizing the ECG data stored at the second memory portion with the map data while continuing to perform the mapping procedure. For example, in response to receiving the request to export the ECG data, the acquired ECG data, being utilized to perform the current mapping procedure, continues to be stored in the first memory portion. In response to receiving the request, however, the storing of the acquired ECG data in the second memory portion is stopped.

In addition, the ECG data currently stored in the second memory portion is synchronized with the map data (e.g., map data 402). For example, ECG data corresponding to one or more acquired signals may be deleted from the ECG map data or added to (e.g., from another map) the ECG map data during the mapping procedure prior to receiving the request to export the ECG data. The ECG data currently stored in the second memory portion (e.g., the removable storage device) is synchronized with the ECG map data such that the ECG data currently stored in the second memory portion matches the ECG map data generated prior to receiving the request to export the ECG data. The synchronization of the ECG data currently stored in the second memory portion and the ECG map data is then verified (e.g., automatically by processing device 204 or manually).

The removable device, which includes the exported ECG data, is removed from the first computing device. The removable device may then be imported to another computing device (not shown), remote from the computing device 216. The ECG data is processed at the other computing device according to user defined algorithms. Resulting data resulting from the processing is then stored to the removable storage device to be imported to the computing device 216.

For example, after the ECG data is synchronized and exported, the storage device may be removed from the first computing device and inserted into the second computing device remote from the first computing device. Additional procedures (e.g., using user-defined algorithms) may be performed at the second computing device which provide new values (e.g., user-defined values) for the ECG data corresponding to the acquired electrical signals (i.e., ECG acquisition points).

Figure 5:
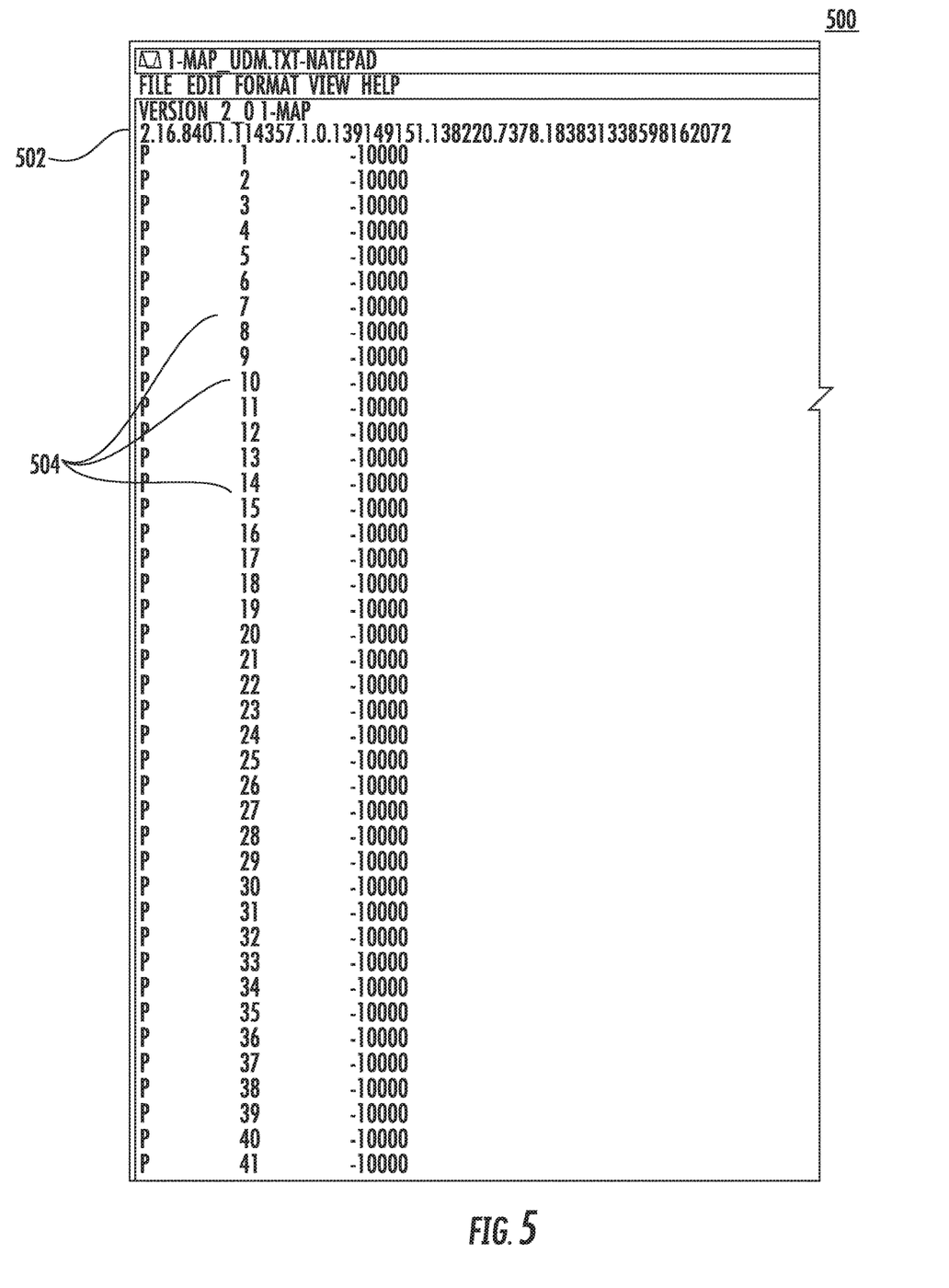
FIG. 5 is a screen shot of a display of user defined values to be provided to a plurality of ECG data acquisition points stored in an exported folder.

FIG. 5 is a screen shot illustrating new ECG data, provided by a user for each of the acquired electrical signals. The new ECG data includes new values 502, to replace the values of the exported ECG data stored in the exported folder of the removable storage device. FIG. 5 also shows default values of "−10000" for LATs corresponding to each of the acquisition points 504.

As shown at block 312, the method 300 includes importing new ECG data from the second memory portion. The new ECG data, resulting from the user-defined values (e.g., values 502 in FIG. 5), is imported back into the first computing device with the new ECG data.

The new data stored in the exported folder, having the name of the map and study, may be imported via a request to import the new data. For example, the request may be a user request received via the user interface at the first computing device. The imported folder is saved, for example, at a higher level (e.g., "MediaStorageDevice\UserDefinedMap") folder than the sub-folder.

As shown at block 314, the method 300 includes displaying a new map using the new map data. For example, when the new ECG data is received (e.g., by processing device 204), the mapping procedure, which has continued while the new data was generated at the second computing device, generates new map data from the new ECG data and a new map is displayed (e.g., on the display device 206) using the new map data.

Referring again to FIG. 4, the example display 400 includes a UDM indicator bar 408 which includes a plurality of different indicators, each indicating a value for one or more corresponding points. As shown in FIG. 4, the exemplary UDM indicator bar 408 includes values ranging from 1.00 to 6.00. The indicators on the UDM indicator bar 408 and on the heart map 404 change according to the imported new ECG data. The new data (e.g., UDM values) 410 is displayed on the left side of display 400 in a UDM column, each value corresponding to one of the ECG data acquisition points (i.e., each signal). For example, as shown in FIG. 4, a new value of 1 (corresponding to the value of 1.00 at left most side of the UDM indicator bar 408) is imported for point 001. New values are also imported for points 002-006. For example, a new value of 6 (corresponding to the value of 6.00 at the right most side of indicator bar 408) is imported for point 006. Embodiments may include indicators different from those shown in FIG. 4, such as for example, different colors corresponding to different values. Embodiments may also include a different number of indicators from those shown in FIG. 4.

The methods provided can be implemented in a general purpose computer, a processor, or a processor core. Suitable processors include, by way of example, a general purpose processor, a special purpose processor, a conventional processor, a digital signal processor (DSP), a plurality of microprocessors, one or more microprocessors in association with a DSP core, a controller, a microcontroller, Application Specific Integrated Circuits (ASICs), Field Programmable Gate Arrays (FPGAs) circuits, any other type of integrated circuit (IC), and/or a state machine. Such processors can be manufactured by configuring a manufacturing process using the results of processed hardware description language (HDL) instructions and other intermediary data including netlists (such instructions capable of being stored on a computer readable media). The results of such processing can be maskworks that are then used in a semiconductor manufacturing process to manufacture a processor which implements features of the disclosure.

The methods or flow charts provided herein can be implemented in a computer program, software, or firmware incorporated in a non-transitory computer-readable storage medium for execution by a general purpose computer or a processor. Examples of non-transitory computer-readable storage mediums include a read only memory (ROM), a random access memory (RAM), a register, cache memory, semiconductor memory devices, magnetic media such as internal hard disks and removable disks, magneto-optical media, and optical media such as CD-ROM disks, and digital versatile disks (DVDs).

It should be understood that many variations are possible based on the disclosure herein. Although features and elements are described above in particular combinations, each feature or element can be used alone without the other features and elements or in various combinations with or without other features and elements.

What is claimed is:

1. An electrocardiogram (ECG) data management system comprising:
   a first memory portion configured to store portions of ECG data, each portion having values corresponding to an electrical signal of a heart of a patient acquired, over a same time period as the other portions, via a corresponding one of a plurality of electrodes disposed at different areas of the heart of the patient; and
   a second memory portion configured to store each portion of the ECG data corresponding to the electrical signals of the heart of the patient acquired over the same time period;
   a processing device configured to manage mapping of the ECG data by:
      performing a mapping procedure including generating and displaying map data corresponding to each portion of the ECG data acquired over the same period of time;

concurrently storing each portion of the ECG data, acquired over the same period of time, in the first memory portion and the second memory portion; and in response to a request to export each portion of the ECG data, stopping the storing of the ECG data in the second memory portion and synchronizing the ECG data stored in the second memory portion with the map data while continuing to perform the mapping procedure.

2. The system of claim 1, wherein the processing device is further configured to manage the mapping of the ECG data by:

importing new ECG data comprising new values which replace values of the map data; and performing the mapping procedure by generating new map data from the new ECG data and providing the new map data for displaying a new map.

3. The system of claim 1, further comprising a catheter which comprises the plurality of electrodes, wherein the catheter is maneuverable to place each of the plurality of electrodes at the different areas of the heart.

4. The system of claim 1, wherein the second memory portion is a removable storage device.

5. The system of claim 1, wherein the processing device is further configured to manage mapping of the ECG data by:

providing a plurality of selectable acquisition time intervals, each comprising a different time period for acquiring the electrical signals of the heart;

receiving a selection to acquire the electrical signals of the heart using one of the plurality of selectable acquisition time intervals; and acquiring the electrical signals of the heart using one of the plurality of selectable acquisition time intervals for the mapping procedure.

6. The system of claim 1, wherein synchronizing the ECG data stored in the second memory portion with the map data comprises causing the ECG data currently stored in the second memory portion to match the map data generated prior to receiving the request to export the ECG data.

7. The system of claim 6, wherein causing the ECG data currently stored in the second memory portion to match the map data generated prior to receiving the request to export the ECG data further comprises at least one of deleting a current portion of the ECG data stored in the second memory portion and adding an additional portion of ECG data to the ECG data stored in the second memory portion.

8. The system of claim 6, further comprising a display device, wherein the processing device is further configured to manage mapping of the ECG data by providing the map data and the one or more maps to the display device for display, and the display device is configured to display at least one of the map data and the one or more maps.

9. A method of managing electrocardiogram ECG data for a user defined map, the method comprising:

acquiring portions of ECG data, each portion corresponding to an electrical signal of a heart acquired over a same time period as the other portions, via a corresponding one of a plurality of electrodes disposed at different areas of the heart;

performing a mapping procedure including generating and displaying map data corresponding to each portion of the ECG data acquired over the same period of time;

concurrently storing each portion of the ECG data, acquired over the same period of time, in a first memory portion and a second memory portion; and in response to a request to export each portion of the ECG data, stopping the storing of the ECG data in the second memory portion and synchronizing the ECG data stored in the second memory portion with the map data while continuing to perform the mapping procedure.

10. The method of claim 9, further comprising:

importing new ECG data comprising new values which replace values of the map data; and performing the mapping procedure by generating new map data from the new ECG data and providing the new map data for displaying a new map; and displaying the new map data and the new map.

11. The method of claim 9, further comprising:

providing a plurality of selectable acquisition time intervals, each comprising a different time period for acquiring the electrical signals of the heart;

receiving a selection to acquire the electrical signals of the heart using one of the plurality of selectable acquisition time intervals; and acquiring the electrical signals of the heart using one of the plurality of selectable acquisition time intervals for the mapping procedure.

12. The method of claim 9, wherein synchronizing the ECG data stored in the second memory portion with the map data comprises causing the ECG data currently stored in the second memory portion to match the map data generated prior to receiving the request to export the ECG data.

13. The method of claim 12, wherein causing the ECG data currently stored in the second memory portion to match the map data generated prior to receiving the request to export the ECG data further comprises at least one of deleting a current portion of the ECG data stored in the second memory portion and adding an additional portion of ECG data to the ECG data stored in the second memory portion.

14. The method of claim 9, further comprising:

providing the map data and the one or more maps to a display device for display, and displaying at least one of the map data and the one or more maps at the display device.

15. The method of claim 9, further comprising using a catheter comprising the plurality of electrodes to acquire the electrical signals of the heart.

16. A non-transitory computer readable medium comprising instructions for causing a computer to execute a computer vision acceleration method, the instructions comprising:

acquiring portions of ECG data, each portion corresponding to an electrical signal of a heart acquired over a same time period as the other portions, via a corresponding one of a plurality of electrodes disposed at different areas of the heart;

performing a mapping procedure including generating and displaying map data corresponding to each portion of the ECG data acquired over the same period of time;

concurrently storing each portion of the ECG data, acquired over the same period of time, in a first memory portion and a second memory portion; and in response to a request to export each portion of the ECG data, stopping the storing of the ECG data in the second memory portion and synchronizing the ECG data stored in the second memory portion with the map data while continuing to perform the mapping procedure.

17. The computer readable medium of claim 16, the instructions further comprising:
importing new ECG data comprising new values which replace values of the map data; and
performing the mapping procedure by generating new map data from the new ECG data and providing the new map data for displaying a new map; and
displaying the new map data and the new map.

18. The computer readable medium of claim 16, the instructions further comprising:
providing a plurality of selectable acquisition time intervals, each comprising a different time period for acquiring the electrical signals of the heart;
receiving a selection to acquire the electrical signals of the heart using one of the plurality of selectable acquisition time intervals; and
acquiring the electrical signals of the heart using one of the plurality of selectable acquisition time intervals for the mapping procedure.

19. The computer readable medium of claim 16, wherein synchronizing the ECG data stored in the second memory portion with the map data comprises causing the ECG data currently stored in the second memory portion to match the map data generated prior to receiving the request to export the ECG data.

20. The computer readable medium of claim 16, wherein causing the ECG data currently stored in the second memory portion to match the map data generated prior to receiving the request to export the ECG data further comprises at least one of deleting a current portion of the ECG data stored in the second memory portion and adding an additional portion of ECG data to the ECG data stored in the second memory portion.

* * * * *

UNITED STATES PATENT AND TRADEMARK OFFICE
CERTIFICATE OF CORRECTION

PATENT NO. : 10,842,399 B2
APPLICATION NO. : 15/679632
DATED : November 24, 2020
INVENTOR(S) : Gal Hayam et al.

It is certified that error appears in the above-identified patent and that said Letters Patent is hereby corrected as shown below:

On the Title Page
In Item (72), under "Inventors", in Column 1, Line 1, delete "Kiryat Tivon (IL);" and insert -- Kiryat Tiv'on (IL); --, therefor.
In Item (72), under "Inventors", in Column 1, Line 2, delete "Kiryat Tivon (IL);" and insert -- Kiryat Tiv'on (IL); --, therefor.
In Item (72), under "Inventors", in Column 1, Lines 3-4, delete "Zichron Ya'akov (IL);" and insert -- Zikhron Ya'akov (IL); --, therefor.

In the Drawings
In Fig. 5, Sheet 5 of 5, in Line 1, delete "NATEPAD" and insert -- NOTEPAD --, therefor.

In the Specification
In Column 3, Line 24, delete "mutantis," and insert -- mutandis, --, therefor.
In Column 4, Line 42, delete "2009/0138007)" and insert -- 2009/0138007), --, therefor.

In the Claims
In Column 11, Line 50, in Claim 8, delete "claim 6," and insert -- claim 1, --, therefor.
In Column 11, Line 51, in Claim 8, delete "wherein" and insert -- wherein: --, therefor.

Signed and Sealed this
Seventh Day of February, 2023

Katherine Kelly Vidal
*Director of the United States Patent and Trademark Office*